United States Patent
Hamamoto et al.

(10) Patent No.: US 9,187,580 B2
(45) Date of Patent: Nov. 17, 2015

(54) RESIN PARTICLE HAVING MANY RECESSES ON THE SURFACE THEREOF

(75) Inventors: Shigeki Hamamoto, Himeji (JP); Hirotsugu Kawata, Himeji (JP); Kiyoshi Yamaguchi, Himeji (JP); Masayoshi Okubo, Kobe (JP)

(73) Assignee: SUMITOMO SEIKA CHEMICALS CO., LTD., Hyogo (JP)

(*) Notice: Subject to any disclaimer, the term of this patent is extended or adjusted under 35 U.S.C. 154(b) by 413 days.

(21) Appl. No.: 12/991,010

(22) PCT Filed: May 11, 2009

(86) PCT No.: PCT/JP2009/058746
§ 371 (c)(1),
(2), (4) Date: Dec. 10, 2010

(87) PCT Pub. No.: WO2009/142119
PCT Pub. Date: Nov. 26, 2009

(65) Prior Publication Data
US 2011/0090568 A1    Apr. 21, 2011

(30) Foreign Application Priority Data

May 21, 2008  (JP) .................................. 2008-133144

(51) Int. Cl.
| | |
|---|---|
| B32B 5/16 | (2006.01) |
| B32B 9/00 | (2006.01) |
| B32B 9/04 | (2006.01) |
| B32B 27/00 | (2006.01) |
| B32B 27/30 | (2006.01) |
| C08F 8/00 | (2006.01) |
| C08F 30/08 | (2006.01) |
| C08F 130/08 | (2006.01) |
| C08F 230/08 | (2006.01) |
| C08F 2/44 | (2006.01) |
| A61K 8/895 | (2006.01) |
| A61Q 19/00 | (2006.01) |
| C08F 20/18 | (2006.01) |
| C08F 220/28 | (2006.01) |
| G02B 5/02 | (2006.01) |
| C08F 271/02 | (2006.01) |
| C08F 212/08 | (2006.01) |

(52) U.S. Cl.
CPC . *C08F 2/44* (2013.01); *A61K 8/895* (2013.01); *A61Q 19/00* (2013.01); *B32B 5/16* (2013.01); *B32B 9/045* (2013.01); *B32B 27/308* (2013.01); *C08F 8/00* (2013.01); *C08F 20/18* (2013.01); *C08F 220/28* (2013.01); *C08F 230/08* (2013.01); *C08F 271/02* (2013.01); *G02B 5/0242* (2013.01); *G02B 5/0278* (2013.01); *C08F 212/08* (2013.01); *C08F 2800/20* (2013.01); *C08F 2810/20* (2013.01); *C08F 2810/50* (2013.01)

(58) Field of Classification Search
CPC ........ B32B 5/16; B32B 9/045; B32B 27/308;
A61K 8/895; A61Q 19/00; C08F 2/44;
C08F 8/00; C08F 20/18; C08F 212/08;
C08F 220/28; C08F 230/08; C08F 2800/20;
C08F 2810/20; C08F 2810/50; C08F 271/02;
G02B 5/0242; G02B 5/0278
USPC ...................... 525/326.1, 326.3, 326.5, 902;
428/402.24, 447, 500
See application file for complete search history.

(56) References Cited

U.S. PATENT DOCUMENTS

| | | | | |
|---|---|---|---|---|
| 3,914,338 | A  * | 10/1975 | Krieg et al. ..................... | 525/77 |
| 5,023,159 | A  * | 6/1991 | Ong et al. .................. | 430/110.2 |
| 8,703,865 | B2 * | 4/2014 | Ganschow et al. ........... | 524/801 |
| 2003/0204013 | A1 | 10/2003 | Swarup et al. | |
| 2008/0020207 | A1 | 1/2008 | Hashiba et al. | |

FOREIGN PATENT DOCUMENTS

| | | |
|---|---|---|
| CN | 1059913 A | 4/1992 |
| EP | 0 448 391 A2 | 9/1991 |
| EP | 1775640 A1 | 4/2007 |

(Continued)

OTHER PUBLICATIONS

Supplementary European Search Report dated May 11, 2011, issued in corresponding European Patent Application No. 09750481.5.

(Continued)

*Primary Examiner* — Patrick Niland
(74) *Attorney, Agent, or Firm* — Westerman, Hattori, Daniels & Adrian, LLP

(57) ABSTRACT

The present invention provides a resin particle having many recesses on the surface thereof, which has solvent resistance and heat resistance. More specifically, the present invention provides a resin particle having many recesses on the surface thereof which is obtained by using a seed particle, wherein a seed particle component in the resin particle has a crosslinked structure. Since the resin particle having many recesses on the surface thereof of the present invention is excellent in solvent resistance and heat resistance in addition to light diffusing properties, the resin particle is appropriate for use, for example, in not only cosmetics containing silicone oil and the like in a preparation, a light diffusing film and a light diffusing sheet prepared by dispersing resin particles as a light diffusing agent in an organic solvent such as 2-butanone and the like in a production process, and a light diffusing plate prepared by kneading at a high shear force the resin particles as a light diffusing agent with polystyrene or polymethyl methacrylate and the like which melts at a high temperature of approximately 300° C. in a production process.

6 Claims, 2 Drawing Sheets

(56) References Cited

FOREIGN PATENT DOCUMENTS

| | | | |
|---|---|---|---|
| JP | 64-000133 | A | 1/1989 |
| JP | 05-331215 | A | 12/1993 |
| JP | 10-007704 | A | 1/1998 |
| JP | 2002-179708 | A | 6/2002 |
| JP | 2002-226708 | A | 6/2002 |
| JP | 2003-226708 | A | 8/2003 |
| JP | 2005-171096 | A | 6/2005 |
| JP | 2005-523351 | A | 8/2005 |
| JP | 2006-143968 | A | 6/2006 |
| KR | 1020070032663 | A | 3/2007 |
| WO | 03/089477 | A1 | 10/2003 |
| WO | WO 2005/105931 | * | 11/2005 |

OTHER PUBLICATIONS

International Search Report of PCT/JP2009/058746, mailing date Jul. 21, 2009.

Notification of Transmittal of Translation of the International Preliminary Report on Patentability (Form PCT/IB/338) of International Application No. PCT/JP2009/058746 mailed Jan. 20, 2011 with Forms PCT/IB/373 and PCT/ISA/237.

Chinese Office Action dated May 15, 2012, issued in corresponding Chinese Patent Application No. 200980118307.9.(5 pages).

Korean Office Action dated Apr. 13, 2015, issued in corresponding KR Patent Aplication No. 10-2010-7025950 (4 pages).

* cited by examiner

RESIN PARTICLE HAVING MANY RECESSES ON THE SURFACE THEREOF

TECHNICAL FIELD

The present invention relates to a resin particle having many recesses on the surface thereof, more specifically, to a resin particle having many recesses on the surface thereof which can be appropriately used in a light diffusing film, a light diffusing sheet and a light diffusing plate, as well as a light diffusing agent as their materials and a cosmetic and the like.

BACKGROUND ART

In recent years, it has been considered to use resin particles having many recesses on the surface thereof in fields of a light diffusing agent, a light diffusing film, a light diffusing sheet, a light diffusing plate, and cosmetics which use the same because of a unique form of the resin particles.

Conventionally, a resin particle having many recesses on the surface, for example, obtained by a method comprising performing a seed dispersion polymerization of an aromatic vinyl monomer in a solvent wherein spherical particles of a methacrylate ester polymer are dispersed as seed particles, and drying the polymer, has been known as resin particles having many recesses on the surface thereof (see Patent Document No. 1).

However, resin particles having many recesses have problems, for example, upon using them as a light diffusing agent in a light diffusing film, a light diffusing sheet, a light diffusing plate and the like, in a case where they are applied on a film-like or sheet-like resin, resin particles dissolve to disappear in a solvent which is binder; in a case where a plate is formed by mixing and dispersing them into matrix resin, resin particles melt to disappear; and the like.

Accordingly, a resin particle having many recesses on the surface thereof, which possesses solvent resistance and heat resistance, has been expected.

Patent Document 1

JP 2002-179708

SUMMARY OF THE INVENTION

The purpose of the present invention is to provide a resin particle having many recesses on the surface thereof, which possesses solvent resistance and heat resistance.

Namely, the present invention relates to a resin particle having many recesses on the surface thereof, obtained by using a seed particle, wherein a component part of the seed particle for the resin particle has a crosslinked structure.

According to the present invention, a resin particle having many recesses on the surface thereof, which possesses solvent resistance and heat resistance, can be provided.

BEST MODE FOR CARRYING OUT THE INVENTION

Figure 1:
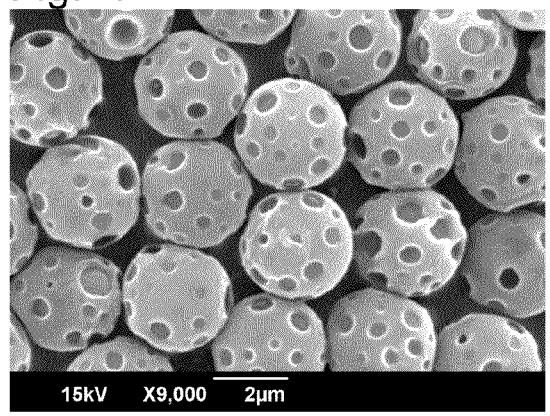
FIG. 1 is an electron micrograph of resin particles having many recesses on the surface thereof in Example 1.

The resin particle having many recesses on the surface thereof according to the present invention is a resin particle obtained by using a seed particle, wherein a component part of the seed particle for the resin particle has a crosslinked structure.

Examples of the crosslinked structure include, but not limited to, a crosslinked structure of a carboxyl group with a glycidyl group, a hydroxyl group, an amino group, an oxazoline, an oxetane, a carbonate, a hydroxy alkyl amide, an aluminium halide, an azetidinium, an isocyanate, a halohydrin, an alkoxy silane, etc.; a crosslinked structure of an alcohol with a glycidyl group and an isocyanate; a self-crosslinked structure of glycidyl groups; a siloxane bond crosslinked structure of silyl groups; and the like.

In the present invention, the siloxane bond crosslinked structure of silyl groups is more specifically explained as an example of an embodiment.

It is preferable that a seed particle prepared from monomers having a silyl group so that a component part of a seed particle for the resin particle having many recesses has a siloxane bond crosslinked structure.

The monomer having a silyl group includes, for example, a compound having a silyl group represented by the formula (1):

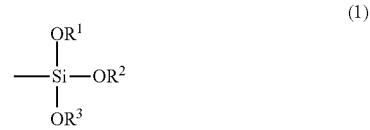

wherein $R^1$ to $R^3$ each independently represent a hydrogen atom, or an alkyl group having a carbon number of 1 to 5.

The alkyl group having a carbon number of 1 to 5 includes, for examples, a methyl group, an ethyl group, a n-propyl group, a n-butyl group, a n-pentyl group and the like.

Examples of the monomer having a silyl group used in the present invention include, for example, vinyl compounds such as vinyl trimethoxy silane, vinyl triethoxysilane and etc.; epoxy compounds such as 2-(3,4-epoxycyclohexyl)ethyl trimethoxy silane, 3-glycidoxypropyl trimethoxysilane, 3-glycidoxypropyl methyl diethoxysilane, 3-glycidoxypropyl triethoxysilane and etc.; styryl compounds such as p-styryl trimethoxysilane and etc.; (meth)acryloxy compounds [hereinafter, "acryloxy" and "methacryloxy" are integrally referred to as "(meth)acryloxy"] such as 3-(meth)acryloxypropyl methyl dimethoxysilane, 3-(meth)acryloxypropyl trimethoxysilane, 3-(meth)acryloxypropyl methyl diethoxysilane, 3-(meth)acryloxypropyl triethoxysilane, etc.; amino compounds such as N-2-(aminoethyl)-3-aminopropyl methyl dimethoxysilane, N-2-(aminoethyl)-3-aminopropyl trimethoxysilane, N-2-(aminoethyl)-3-aminopropyl triethoxysilane, 3-aminopropyl trimethoxysilane, 3-aminopropyl triethoxysilane, 3-triethoxysilyl-N-(1,3-dimethyl-butylidene) propylamine, N-phenyl-3-aminopropyl trimethoxysilane, etc.; ureide compounds such as 3-ureidopropyl triethoxysilane etc.; chloropropyl compounds such as 3-chloropropyl trimethoxysilane etc.; mercapto compounds such as 3-mercaptopropyl methyl dimethoxysilane, 3-mercaptopropyl trimethoxysilane, etc.; sulfide compounds such as bis(triethoxysilylpropyl)tetrasulfide, etc.; and isocyanate compounds such as 3-isocyanate propyltriethoxysilane, etc. Among such monomers, (meth)acryloxy compounds such as 3-(meth) acryloxypropyl methyl dimethoxysilane, 3-(meth)acryloxypropyl trimethoxysilane, 3-(meth)acryloxypropyl methyl diethoxysilane, 3-(meth)acryloxypropyl triethoxysilane, etc. are preferably used from the viewpoints of reactivity and solubility to reaction solvents of the monomer having a silyl group upon producing the seed particle. These monomers having a silyl group may be used alone or in combination of two or more kinds thereof.

The resin particle having many recesses on the surface thereof of the present invention can be obtained by a method which comprises obtaining a resin particle precursor having many recesses on the surface thereof by seed polymerizing a seed particle constituted with the monomer having a silyl group as a constitutive monomer component in the presence of monomers for seed polymerization, and by crosslinking the silyl groups via a chemical reaction to form siloxane bonds, and the like.

A process for producing a seed particle in which the monomer having a silyl group used in the present invention is used as a constitutive monomer component, but not especially limited to, includes, for example, polymerization methods such as a conventionally-known emulsion polymerization or dispersion polymerization and the like.

In the present specification, a dispersion polymerization method is explained in more detail as one embodiment. In this method, a polymerization reaction of the monomer having a silyl group and, optionally other monomers are performed in a reaction solvent containing a dispersing agent by using a polymerization initiator.

Examples of the other monomers include (meth)acrylic esters such as methyl (meth)acrylate [hereinafter, "acryloxy" and "methacryloxy" are integrally referred to as "(meth)acryloxy"], ethyl (meth)acrylate, propyl (meth) acrylate, butyl (meth) acrylate, n-hexyl (meth) acrylate, cyclohexyl (meth) acrylate, 2-ethylhexyl (meth) acrylate, dodecyl (meth)acrylate, stearyl (meth)acrylate, etc.; vinyl esters such as vinyl acetate, vinyl propionate, etc.; aromatic vinyls such as styrene, α-methylstyrene, vinyltoluene, dimethylstyrene, etc.; and olefins such as ethylene, propylene, etc. Among such other monomers, methyl (meth)acrylate, butyl (meth)acrylate and styrene are preferably used from the viewpoints of enhancing solvent resistance and heat resistance of the resulting resin particle having many recesses on the surface thereof. These other monomers may be used alone or in combination of two or more kinds thereof.

The amount of the other monomers to be used is preferably 100 to 900 parts by mass, more preferably 150 to 900 parts by mass to 100 parts by mass of the monomer having a silyl group. When the amount of the other monomers to be used is less than 100 parts by mass, the resulting seed particles are prone to aggregate. Moreover, when the amount of the other monomers to be used exceeds 900 parts by mass, the solvent resistance and heat resistance of the resulting resin particle having many recesses on the surface thereof are prone not to be enhanced sufficiently.

Examples of the polymerization initiator include azo compounds such as 2,2'-azobis(2-methylpropionitrile), 1,1'-azobis(cyclohexane 1-carbonitrile), etc.; peroxides such as dibenzoyldioxidane, 2,4-dichlorobenzoyl peroxide, t-butyl peroxypivalate, 3,5,5-trimethylhexanoyl peroxide, octanoyl peroxide, decanoyl peroxide, lauroyl peroxide, succinic acid peroxide, acetyl peroxide, t-butyl peroxy-2-ethylhexanoate, m-toluoyl peroxide, benzoyl peroxide, t-butyl peroxymaleic acid, t-butyl peroxylaurate, t-butyl peroxy-3,5,5-trimethyl hexanoate, cyclohexanone peroxide, t-butyl peroxyisopropyl carbonate, 2,5-dimethyl-2,5-di(benzoylperoxy)hexane, 2,2-bis(t-butylperoxy)octane, t-butyl peroxyacetate, 2,2-bis(t-butyl peroxy)butane, t-butyl peroxybenzoate, n-butyl-4,4-bis (t-butyl peroxy)valerate, di-t-butyl-diperoxyisophtalate, methylethylketone peroxide, dicumyl peroxide, 2,5-dimethyl-2,5-di(t-butylperoxy)hexane, t-butyl cumylperoxide, and the like. Among such polymerization initiators, 2,2'-azobis(2-methylpropionitrile), 1,1'-azobis(cyclohexane 1-carbonitrile), and dibenzoyldioxidane from the viewpoint of easiness in polymerization reaction control, and 2,2'-azobis(2-methylpropionitrile) and 1,1'-azobis(cyclohexane 1-carbonitrile) are preferably used from the viewpoint of safety of substances. These polymerization initiators may be used alone or in combination of two or more kinds thereof.

The amount of the polymerization initiators to be used is preferably 0.5 to 5 parts by mass, more preferably 0.8 to 4 parts by mass to 100 parts by mass of all the monomers to be used in the production of a seed particle. When the amount of the polymerization initiators to be used is less than 0.5 parts by mass, the polymerization reaction is prone to require great time. Moreover, when the amount of the polymerization initiator to be used exceeds 5 parts by mass, a rapid polymerization reaction is prone to occur, and besides the monomer used in the production of a seed particle is prone to decompose.

Examples of the dispersing agent include xanthan gum, guar gum, carboxymethylcellulose, polyvinyl pyrrolidone, carboxy vinyl polymer, polyacrylic acid, polyvinyl alcohol, polyethylene glycol, polyethylene oxide, starch derivatives, polysaccharides, and the like. Among such dispersing agents, polyvinyl pyrrolidone and polyacrylic acid are preferably used from the viewpoints of solubility to a reaction solvent, stability of a polymerization reaction, and particle diameter control of a seed particle. These dispersing agents may be used alone or in combination of two or more kinds thereof.

The amount of the dispersing agent to be used is preferably 30 to 100 parts by mass, more preferably 50 to 80 parts by mass to 100 parts by mass of all the monomers used in the production of a seed particle. When the amount of the dispersing agent to be used is less than 30 parts by mass, the resulting seed particles are prone to aggregate. Moreover, when the amount of the dispersing agent to be used exceeds 100 parts by mass, the dispersing agent is prone not to dissolve in a reaction solvent.

Examples of the reaction solvent include acetone, acetonitrile, N,N-dimethylformamide, dimethyl sulfoxide, 1-butanol, 2-propanol, 1-propanol, ethanol, methanol, water, etc. Among such reaction solvents, methanol and ethanol are preferably to be used from the viewpoints of solubility of a monomer to be used in the production of a seed particle, and stability of a polymerization reaction. These reaction solvents may be used alone or in combination of two or more kinds thereof.

The amount of the reaction solvent to be used is preferably 200 to 1,500 parts by mass, more preferably 500 to 1000 parts by mass to 100 parts by mass of all the monomers to be used in the production of a seed particle. When the amount of the reaction solvent to be used is less than 200 parts by mass, the monomer used in the production of a seed particle is prone not to dissolve. Moreover, when the amount of the reaction solvent to be used exceeds 1500 parts by mass, the reaction is prone to become difficult to proceed.

The reaction temperature for polymerization reaction is preferably 20 to 100° C., more preferably 40 to 80° C. from the viewpoints of raising a polymerization reaction rate, and besides smoothly proceeding a polymerization reaction. Reaction time is usually 12 to 48 hours.

Thus, dispersion polymerization is performed to obtain a seed particle constituted with the monomer having a silyl group as a constitutive monomer component.

In the present invention, a resin particle precursor having many recesses on the surface thereof can be obtained, for example, by seed-polymerizing a seed particle constituted with the monomer having a silyl group as a constitutive monomer component, in the presence of monomers for seed polymerization. The seed polymerization method includes, but not especially limited to, for example, seed polymerization methods such as a seed emulsion polymerization method, a seed dispersion polymerization method, and the like.

In the present specification, the seed dispersion polymerization method is explained in more detail as one embodiment. In this method, a resin particle precursor having many recesses can be obtained by seed dispersion polymerising monomers for seed polymerising in a solvent(S1) in which a seed particle constituted with the monomer having a silyl group [hereinafter may be simply referred to as "a seed particle or seed particles"] as a constitute monomer component and by drying them. In this case, it is preferred that the monomer for seed polymerization which will form a recess part, is soluble in the solvent (S1), and that the monomer for seed polymerization is a polymer of monomers having an affinity to the solvent (S1) lower than or equal to that of the seed particle. For example, methanol/water mixed solvent is used as the solvent (S1). The polymerization reaction is preferably performed in the copresence of an organic solvent (S2) which is a poor solvent or non-solvent to a polymerization initiator, a dispersing agent and the seed particle, but is a good solvent to the seed polymerization monomers and is immiscible or partially miscible in the above-mentioned solvent (S1).

Examples of the solvent (S1) include acetone, acetonitrile, N,N-dimethylformamide, dimethyl sulfoxide, 1-butanol, 2-propanol, 1-propanol, ethanol, methanol, water, and the like. Among such solvents, methanol, ethanol and water are preferably used from the viewpoints of solubility of a monomer for seed polymerization and stability of a polymerization reaction, and more preferably methanol/water mixed solvent is used. These solvents (S1) may be used alone or in combination of two or more kinds thereof.

The amount of the solvent (S1) to be used is preferably 500 to 2,500 parts by mass, more preferably 1,000 to 2,000 parts by mass to 100 parts by mass of the seed particle to be used. When the amount of the solvent (S1) to be used is less than 500 parts by mass, the monomer for seed polymerization is prone not to dissolve. Moreover, when the amount of the solvent (S1) to be used exceeds 2,500 parts by mass, the reaction is prone to become difficult to proceed.

Examples of the monomer for seed polymerization include (meth)acrylate alkyl esters having a carbon number of 1 to 8 such as methyl (meth) acrylate, ethyl (meth) acrylate, propyl (meth)acrylate, butyl (meth)acrylate, etc.; aromatic vinyls such as styrene, α-methylstyrene, vinyltoluene, dimethylstyrene, etc.; olefins such as ethylene, propylene, etc.; and the like. Among such monomers for seed polymerization, butyl (meth)acrylate, ethyl (meth)acrylate, and styrene are preferably used from the viewpoint of solubility to the solvent (S1) and stability of the polymerization reaction. These monomers for seed polymerization may be used alone or in combination of two or more kinds thereof.

The amount of the monomer to be used for seed polymerization is preferably 20 to 100 parts by mass, more preferably 30 to 80 parts by mass to 100 parts by mass of the seed particle to be used. When the amount of the monomer to be used for seed polymerization used is less than 20 parts by mass, recesses are prone not to be formed on a seed particle surface. Moreover, when the amount of the monomer to be used for seed polymerization exceeds 100 parts by mass, recesses are prone not to be formed because a seed particle surface is covered.

The organic solvent (S2) is not specifically limited if it is a poor solvent or non-solvent to the seed particle, but it is a good solvent to seed polymerization monomers and is insoluble or partially dissolved in the above-mentioned solvent (S1). Examples of the organic solvent (S2) include decahydronaphthalene, cyclohexane, n-dodecane, limonene, and the like. Among such organic solvents, n-dodecane is preferably used from the viewpoint of the solubility to the polymer produced on the seed particle surface upon seed dispersion polymerization. These organic solvents (S2) may be used alone or in combination of two or more kinds thereof.

The amount of the organic solvent (S2) to be used is preferably 50 to 2,000 parts by mass, more preferably 100 to 1,500 parts by mass to 100 parts by mass of the monomer for seed polymerization. When the amount of the organic solvent (S2) to be used is less than 50 parts by mass, recesses are prone not to be formed on the seed particle surface. Moreover, when the amount of the organic solvent (S2) to be used exceeds 2,000 parts by mass, seed particles are prone to aggregate.

Examples of the polymerization initiator include azo compounds such as 2,2'-azobis(2-methylpropionitrile), 1,1'-azobis(cyclohexane 1-carbonitrile), etc.; peroxides such as dibenzoyldioxidane, 2,4-dichlorobenzoyl peroxide, t-butyl peroxypivalate, 3,5,5-trimethylhexanoyl peroxide, octanoyl peroxide, decanoyl peroxide, lauroyl peroxide, succinic acid peroxide, acetyl peroxide, t-butyl peroxy-2-ethylhexanoate, m-toluoyl peroxide, benzoyl peroxide, t-butyl peroxymaleic acid, t-butyl peroxylaurate, t-butyl peroxy-3,5,5-trimethyl hexanoate, cyclohexanone peroxide, t-butyl peroxyisopropyl carbonate, 2,5-dimethyl-2,5-di(benzoylperoxy)hexane, 2,2-bis(t-butylperoxy)octane, t-butyl peroxyacetate, 2,2-bis(t-butyl peroxy)butane, t-butyl peroxybenzoate, n-butyl-4,4-bis (t-butyl peroxy)valerate, di-t-butyl-diperoxyisophtalate, methylethylketone peroxide, dicumyl peroxide, 2,5-dimethyl-2,5-di(t-butylperoxy)hexane, t-butyl cumylperoxide, and the like. Among such polymerization initiators, from the viewpoint of easiness in polymerization reaction control, 2,2'-azobis(2-methylpropionitrile), 1,1'-azobis(cyclohexane 1-carbonitrile), and dibenzoyldioxidane, from the viewpoint of safety of the substances, 2,2'-azobis(2-methylpropionitrile) and 1,1'-azobis (cyclohexane 1-carbonitrile) are preferably used. These polymerization initiators may be used alone or in combination of two or more kinds thereof.

The amount of the polymerization initiators to be used is preferably 2 to 10 parts by mass, more preferably 5 to 8 parts by mass to 100 parts by mass of the seed particle to be used in the production of a seed particle. When the amount of the polymerization initiators to be used is less than 2 parts by mass, the polymerization reaction is prone to require great time. Moreover, when the amount of the polymerization initiator to be used exceeds 10 parts by mass, not only a rapid polymerization reaction is prone to occur, but also the monomer to be used in the production of a seed particle is prone to decompose.

Examples of the dispersing agent include xanthan gum, guar gum, carboxymethylcellulose, polyvinyl pyrrolidone, carboxy vinyl polymer, polyacrylic acid, polyvinyl alcohol, polyethylene glycol, polyethylene oxide, starch derivatives, polysaccharides, and the like. Among such dispersing agents, polyvinyl pyrrolidone and polyacrylic acid are preferably used in the viewpoints of solubility to a reaction solvent, and stability of a polymerization reaction. These dispersing agents may be used alone or in combination of two or more kinds thereof.

The amount of the dispersing agent to be used is preferably 30 to 100 parts by mass, more preferably 40 to 90 parts by mass to 100 parts by mass of the seed particle to be used. When the amount of the dispersing agent to be used is less than 30 parts by mass, the seed particles are prone to aggregate. Moreover, when the amount of the dispersing agent used exceeds 100 parts by mass, a recess is prone not to be formed on the seed particle surface.

The reaction temperature for seed dispersion polymerization reaction is preferably 20 to 100° C., more preferably 40 to 80° C. from the viewpoints of forming recesses on the seed particle surface, and besides smoothly proceeding a polymerization reaction. Reaction time is usually 12 to 48 hours.

Thus, the seed dispersion polymerization is performed to obtain a resin particle precursor having many recesses on the surface thereof, for example, by washing seed particles with a solvent such as methanol and etc., drying them and gradually releasing the residual solvent from the particles.

In the present invention, the resin particle having many recesses on the surface thereof can be obtained, for example, by crosslinking the silyl groups contained in the resin particle precursor having many recesses on the above-mentioned surface to form siloxane bonds.

The method for forming siloxane bonds from the silyl groups is not especially limited, and siloxane bonds can be formed, for example, by dispersion in a water-containing medium in the presence of an acid catalyst.

Examples of the acid catalyst include paratoluenesulfonic acid, acetic acid, formic acid, citric acid, oxalic acid, and the like. Among such acid catalysts, paratoluenesulfonic acid and acetic acid are preferably used from the viewpoints of solubility to a water-containing medium and a uniform formation of siloxane bonds. These acid catalysts may be used alone or in combination of two or more kinds thereof.

The amount of the acid catalyst to be used is preferably 20 to 100 parts by mass, more preferably 40 to 80 parts by mass to 100 parts by mass of the resin particle precursor having many recesses on the surface thereof from the viewpoint of smoothly proceeding the siloxane bond reaction.

The above-mentioned water-containing medium can be mixed with alcohols such as methanol, ethanol, isopropanol, etc; and hydrophilic organic solvents such as acetonitrile, etc.

The amount of water in the water-containing medium is preferably 50 to 3,000 parts by mass, more preferably 70 to 2,000 parts by mass to 100 parts by mass of the resin particle precursor having many recesses on the surface thereof from the viewpoint of smoothly proceeding a siloxane bond reaction.

Thus, the siloxane bond reaction is performed to obtain a resin particle having many recesses on the surface thereof.

Although the reason why the resin particle having many recesses on the surface thereof of the present invention is excellent in solvent resistance and heat resistance, is unclear, it is presumed as follows. Namely, it is presumed that a layer strong against a solvent or heat is formed because the seed particle component in this resin particle has a crosslinked structure.

Since many recesses are regularly arranged on a surface and a recess part and a particle body are made of different types of resin to form a complex structure, when the resin particle having many recesses on the surface thereof of the present invention is used as a light diffusing agent, it provides an excellent light diffusing agent as well as a light diffusing film, a light diffusing sheet and a light diffusing plate due to a synergy effect of a light diffusing property of the many recesses and a refractive index difference between different types of resin.

Although the content ratio of the resin particle having many recesses on the surface thereof in the light diffusing agent of the present invention is not especially limited, it is desirable to be 1 to 100% by mass, preferably 5 to 100% by mass to the total volume of the light diffusing agent. When the content ratio of the resin particle having many recesses on the surface thereof is less than 1% by mass, a light diffusing property is prone not to be exerted sufficiently.

Moreover, examples of an optional additive mixed with the light diffusing agent include light diffusing agents other than the resin particle having many recesses on the surface thereof; a dye or a pigment, stabilizers such as an antioxidant and etc.; flame retarders; antistatic agents; and the like.

In order to produce a light diffusing plate by using the light diffusing agent of the present invention, for example, there is a method comprising mixing to disperse a light diffusing agent containing the resin particle having many recesses on the surface thereof and optionally other additives in a transparent matrix resin and forming the mixture into a desired shape, for example, by using an extrusion method, injection molding process, and the roll mulling method. Examples of the transparent matrix resin include (meth)acrylic based resins, polycarbonate based resins, styrene based resins, etc.

In addition, in order to produce a light diffusing film or a light diffusing sheet by using the light diffusing agent of the present invention, for example, there is a method comprising applying a light diffusing agent containing the resin particle having many recesses on the surface thereof with a binder on either side or both sides of a matrix resin formed into a film, a sheet and the like. In order to apply a light diffusing agent to a matrix resin, the light diffusing agent is mixed to disperse in for example an organic polymer binder dissolved in a solvent and applying it on the matrix resin. As the applying method, a dipping method, a roll coat method, a screen printing, and the like can be utilized. As the matrix resin, polyethylene terephthalate, polyester, polyamide, polymethylmethacrylate, polycarbonate, polyvinyl chloride, and the like are appropriate. Among such matrix resins, polyethylene terephthalate is appropriately used from the viewpoint of workability and the like. Thickness of the light diffusing layer containing a light diffusing agent is usually 5 to 50 μm, preferably 10 to 30 μm.

Examples of the organic polymer binder include polyester resin, ethylene-vinylacetate copolymer resin, acrylic ester resin, urethane resin and the like. Among such organic polymer binders, polyester resin is appropriately used from the viewpoints of a refractive index, an adhesive property with a matrix, abrasion resistance, transparency and the like.

The mixed amount of a light diffusing agent and an organic polymer binder is usually 50 to 500 parts by mass, preferably 70 to 350 parts by mass of the light diffusing agent to 100 parts by mass of the organic polymer binder. When the mixed amount is within a range of 50 to 500 parts by mass, the decreases in haze and total light transmittance are small.

For the characteristics of the light diffusing film of the present invention, haze is 80% or higher, preferably 85% or higher, and light transmission rate is usually 80% or higher, preferably within a range of 85 to 95%. When haze is lower than 80%, sharpness of screens, for example, in a liquid crystal display and the like is prone to be inferior. When light transmission is lower than 80%, brightness of screens is prone to deteriorate.

EXAMPLES

Although the present invention will be explained with Examples and Comparative Examples in detail below, the present invention is not limited to these examples in any way.

Solvent resistance and heat resistance of the resin particle having many recesses on the surface thereof, obtained in Examples 1-4 and Comparative Examples 1-2, were evaluated by the following methods:

(1) Solvent Resistance

Resin particles having many recesses on the surface thereof were immersed in a beaker into which 2-butanone was placed, and the beaker was capped, and stored at 40° C.

After two months later, the resin particles having many recesses on the surface thereof were removed, and the state of the surface was observed with an electron microscope (JEOL Co., Ltd. Product No. JSM-6390LA). The evaluation results are shown in Table 1.

(2) Heat Resistance

Two parts by mass of the resin particles having many recesses on the surface thereof and 98 parts by mass of polystyrene resin (Toyo Styrene Co. Ltd., article No. HRM40) were mixed and, melt-kneaded at 300° C. Subsequently, it was hot-press molded to prepare a sheet of 2-mm thickness.

Resin particles having many recesses on the surface thereof, which were contained in the sheet, were evaluated with an electron microscope (JEOL Co., Ltd. Product No. JSM-6390LA). The evaluation results are shown in Table 1.

Example 1

Production of a Seed Particle Constituted with a Monomer Having a Silyl Group as a Constitutive Monomer Component One hundred seventy eight grams of methanol, 22 g of styrene, 5.6 g of 3-methacryloxypropyl trimethoxysilane, 18 g of polyvinyl pyrrolidone (K-30) and 0.6 g of 2,2'-azobis(2-methylpropionitrile) were placed into a 500-mL reaction container equipped with a stirrer and an condenser tube, and a polymerization reaction was performed at a stirring rotation speed of 300 rpm, and 60° C. for 24 hours.

After polymerization, the reaction mixture was filtered to obtain 20.2 g of seed particles constituted with a monomer having a silyl group as a constitutive monomer component.

[Production of a Resin Particle Precursor Having Many Recesses on The Surface Thereof]

Into a 500-mL reaction container equipped with a stirrer and a condenser tube, 48.67 g of methanol, and 21.89 g of water were placed, and 4.19 g of the seed particles constituted with a monomer having a silyl group as a constitutive monomer component were dispersed in the mixture. Further, 2.7 g of polyvinyl pyrrolidone (K-30), and 2.625 g of 8% by mass of polyvinyl pyrrolidone (K-90) in a methanol aqueous solution (70% by mass of methanol aqueous solution), 0.1398 g of 2,2'-azobis(2-methylpropionitrile) and 0.0021 g of 1,1'-azobis(cyclohexane 1-carbonitrile) were added.

Under a nitrogen gas atmosphere, a mixed solvent of 2.1 g of n-butyl acrylate and 7.54 g of n-dodecane was continuously added to the mixture over 5 hours at a stirring rotation speed of 300 rpm, and 60° C., and further reacted at the same temperature for 5 hours.

After polymerization, the reaction mixture was filtered, washed with methanol. Subsequently it was dried under vacuum at 25° C. to obtain 5.56 g of a resin particle precursor having many recesses on the surface thereof.

[Production of a Resin Particle Having Many Recesses on the Surface Thereof]

14.35 g of methanol and 26.98 g of water were placed into a 200-mL reaction container equipped with a stirrer and a condenser tube, and 2.50 g of the resin particle precursor having many recesses on the surface thereof was dispersed. Further, 1.518 g of para-toluenesulfonic acid monohydrate was added, and reacted at a stirring rotation speed of 200 rpm, and 60° C. for 3 hours under a nitrogen gas atmosphere.

After the reaction, the reaction mixture was filtered to obtain 2.50 g of a resin particle having many recesses on the surface thereof. The electron micrograph of the resulting resin particles having many recesses on the surface is shown in FIG. 1.

Example 2

According to the same manner as that of Example 1 [Production of a seed particle constituted with a monomer having a silyl group as a constitutive monomer component] except that 5.6 g of 3-methacryloxypropyl trimethoxysilane was substituted with 5.2 g of 3-methacryloxypropyl methyl dimethoxysilane, 2.50 g of resin particles having many recesses on the surface was obtained.

Example 3

According to the same manner as that of Example 1 [Production of a seed particle constituted with a monomer having a silyl group as a constitutive monomer component] except that 5.6 g of 3-methacryloxypropyl trimethoxysilane was substituted with 6.5 g of 3-methacryloxypropyl triethoxysilane, 2.50 g of resin particles having many recesses on the surface was obtained.

Example 4

According to the same manner as that of Example 1 [Production of a seed particle constituted with a monomer having a silyl group as a constitutive monomer component] except that 5.6 g of 3-methacryloxypropyl trimethoxysilane was substituted with 5.3 g of 3-acryloxypropyl trimethoxysilane, 2.50 g of resin particles having many recesses on the surface was obtained.

Comparative Example 1

Five hundreds four grams of methanol, 216 g of purified water, and 54 g of decalin were placed into a 2-L reaction container equipped with a stirrer and a condenser tube, and 1.8 g of polyvinyl pyrrolidone (K-90) was dissolved in the mixture, and 30 g of polymethyl methacrylate spherical particles (an average volume particle diameter of 5 μm) was added, and dispersed. Further, 18 g of styrene, and 1.2 g of 2,2'-azobis(2-methylpropionitrile) were added, and the inner space of the reaction container was made a nitrogen gas atmosphere, and then a polymerization reaction was performed at a stirring rotation speed of 450 rpm, and 60° C. for 24 hours.

Figure 4:
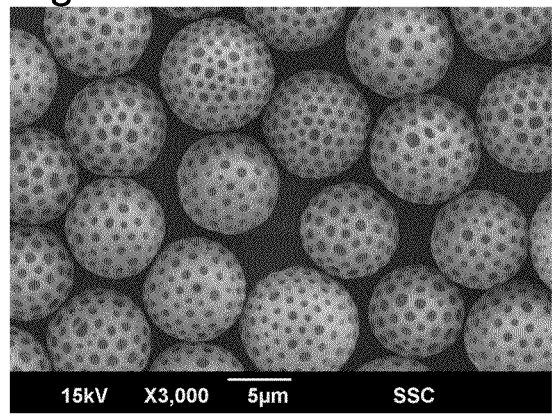
FIG. 4 is an electron micrograph of resin particles having many recesses on the surface thereof of Comparative Example 1.

Solid-liquid separation of the resulting emulsion-like reaction mixture was performed by centrifugal separation, the isolated resin particles were washed with methanol, and then dried under vacuum at 25° C. to obtain 46.5 g of a resin particle precursor having many recesses on the surface thereof. The electron micrograph of the resulting resin particles having many recesses on the surface is shown in FIG. 4.

Comparative Example 2

Two hundreds fifty grams of methanol, 750 g of purified water, and 108 g of styrene were placed into a 2-L reaction container equipped with a stirrer and a condenser tube, and reacted at a stirring rotation speed of 450 rpm, and 70° C. for hours under a nitrogen gas atmosphere to obtain an emulsion of polystyrene particles.

Thirty grams (in solid content conversion) of an emulsion of the polystyrene particles as obtained above was placed into a 2-L reaction container equipped with a stirrer and a condenser tube, 12.9 g of n-butyl acrylate was added, and allowed to stand at 0° C. for 24 hours to absorb n-butyl acrylate into the polystyrene particles to swell the polystyrene particles. Subsequently, 1,000 g of a mixed solvent of ethanol/water (mass ratio: 10/90), and 1 g of potassium persulfate were added, and a polymerization reaction was performed at a stirring rotation speed of 450 rpm, and 70° C. for 24 hours, under a nitrogen atmosphere.

Figure 5:
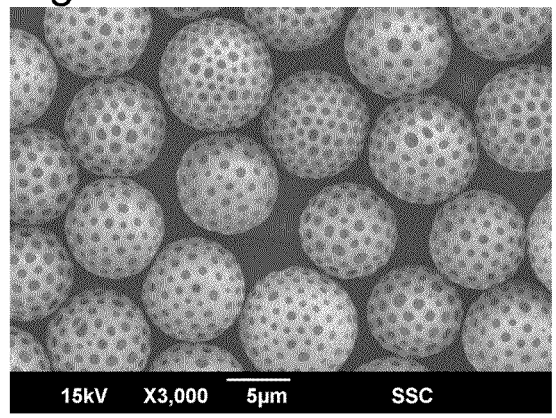
FIG. 5 is an electron micrograph of resin particles having many recesses on the surface thereof of Comparative Example 2.

After polymerization, the reaction mixture was filtered, washed with methanol. Subsequently it was dried at vacuum at 25° C. to obtain 42.9 g of resin particles having many recesses on the surface thereof. The electron micrograph of the resulting resin particle having many recesses on the surface is shown in FIG. 5.

TABLE 1

|  | Solvent resistance | Heat resistance |
| --- | --- | --- |
| Example 1 | Recesses remained. | Recesses remained. |
| Example 2 | Recesses remained. | Recesses remained. |
| Example 3 | Recesses remained. | Recesses remained. |
| Example 4 | Recesses remained. | Recesses remained. |
| Comparative Example 1 | Particles disappeared after 30 min. | Particles merged or dispersed to disappear |
| Comparative Example 2 | Particles disappeared after 30 min. | Particles merged or dispersed to disappear |

Figure 2:
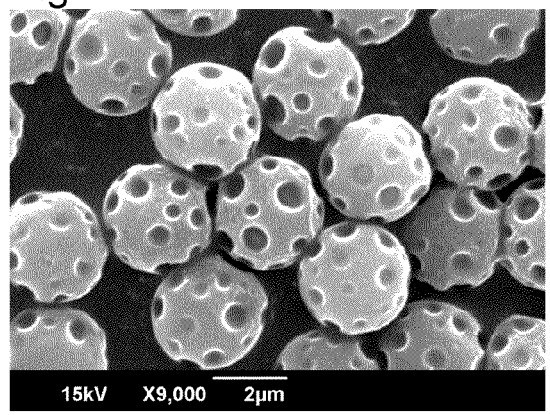
FIG. 2 is an electron micrograph of resin particles having many recesses on the surface thereof of Example 1 after evaluating solvent resistance (at 40° C. for two months).

In solvent resistance evaluation, it was confirmed from an electron micrograph (for example, FIG. 2) that after stored in 2-butanone at 40° C. for two months, the resin particles having many recesses on the surface thereof of Examples 1-4 maintained recesses similarly to those before the evaluation. However, even when the resin particles having many recesses on the surface thereof of Comparative Examples 1 and 2 were stored in 2-butanone at 40° C. only for minutes, the resin particles themselves dissolved to disappear in the solvent.

Figure 3:
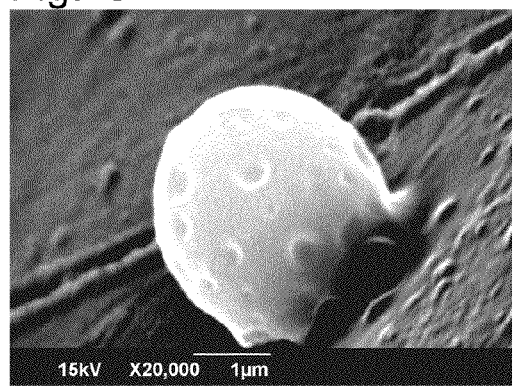
FIG. 3 is an electron micrograph of a resin particle having many recesses on the surface thereof of Example 1 after evaluating heat resistance (melt-kneaded at 300° C., formation of a heat compression-molded sheet).

In heat-resistant evaluation, it was confirmed from an electron micrograph (for example, FIG. 3) that the resin particles having many recesses on the surface thereof of Examples 1-4 maintained the recesses even when a sheet was prepared by hot press molding after melt-kneading at 300° C. However, the resin particles having many recesses on the surface thereof of Comparative Examples 1 and 2 merged or dispersed into the polystyrene resin to disappear.

These results indicate that the resin particle having many recesses on the surface thereof of the present invention is excellent in solvent resistance and heat resistance.

INDUSTRIAL APPLICABILITY

Since the resin particle having many recesses on the surface thereof of the present invention is excellent in solvent resistance and heat resistance in addition to light diffusing properties, the resin particle is appropriate for use, for example, in not only cosmetics containing silicone oil and the like in a preparation, a light diffusing film and a light diffusing sheet prepared by dispersing resin particles as a light diffusing agent in an organic solvent such as 2-butanone and the like in a production process, and a light diffusing plate prepared by kneading at a high shear force the resin particles as a light diffusing agent with polystyrene or polymethyl methacrylate and the like which melts at a high temperature of approximately 300° C. in a production process.

The invention claimed is:

1. A light diffusing agent comprising a resin particle having many recesses on the surface thereof, comprising a seed particle, wherein
a component part of said seed particle has a crosslinked structure;
said seed particle is a resin formed of
at least one monomer having a silyl group selected from the group consisting of 3-(meth)acryloxypropyl methyl dimethoxysilane, 3-(meth)acryloxypropyl trimethoxysilane, 3-(meth)acryloxypropyl methyl diethoxysilane, and 3-(meth)acryloxypropyl triethoxysilane, and
other monomers, wherein an amount of the other monomers used in the resin particle having many recesses on the surface thereof is 100 to 900 parts by mass with respect to 100 parts by mass of the monomer having a silyl group; and
said resin particle is obtained by seed-polymerizing a monomer for seed polymerization in a solvent which is at least one selected from the group consisting of acetone, acetonitrile, N,N-dimethylformamide, dimethyl sulfoxide, 1-butanol, 2-propanol, 1-propanol, ethanol, methanol, and a mixed solvent of water with one or more of the preceding solvents in the presence of said seed particle, and crosslinking at least a part of said seed particle in the presence of said seed particle, and crosslinking at least a part of said seed particle.

2. The light diffusing agent according to claim 1, wherein the method for seed polymerization is a seed dispersion polymerization method.

3. A light diffusing film obtained by applying the light diffusing agent of claim 1 to a film resin with a binder.

4. A light diffusing sheet obtained by applying the light diffusing agent of claim 1 to a sheet resin with a binder.

5. A light diffusing plate obtained by mixing to disperse the light diffusing agent of claim 1 in a transparent matrix resin, and forming it.

6. The light diffusing agent according to claim 1, wherein the solvent is at least one selected from the group consisting of 1-butanol, 2-propanol, 1-propanol, ethanol, methanol, and a mixed solvent of water with one or more of the preceding solvents.

* * * * *